United States Patent
Hagen et al.

(10) Patent No.: US 6,639,102 B2
(45) Date of Patent: Oct. 28, 2003

(54) PROCESS FOR PRODUCING POLYISOCYANATES OF THE DIPHENYL METHANE SERIES HAVING A REDUCED COLOR VALUE

(75) Inventors: Torsten Hagen, Düsseldorf (DE); Friedhelm Kämper, Krefeld (DE); Daniel Koch, Duisburg (DE); Rudolf Uchdorf, Krefeld (DE); Stefan Wershofen, Mönchengladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/384,890

(22) Filed: Mar. 10, 2003

(65) Prior Publication Data

US 2003/0176626 A1 Sep. 18, 2003

(30) Foreign Application Priority Data

Mar. 13, 2002 (DE) .......................... 102 11 021

(51) Int. Cl.$^7$ ..................... C07C 263/10; C07C 263/18; C07C 263/20; C07C 209/82; C07C 209/90
(52) U.S. Cl. ..................... 560/347; 560/336; 560/352; 560/359; 564/330; 564/331; 564/333; 564/334; 564/409; 564/426; 564/427; 564/437; 564/438; 252/182.13; 252/182.29
(58) Field of Search ................. 560/336, 347, 560/352, 359; 564/330, 331, 333, 334, 409, 426, 427, 437, 438; 252/182.13, 182.29

(56) References Cited

U.S. PATENT DOCUMENTS

| | | | | | |
|---|---|---|---|---|---|
| 4,025,557 | A | * | 5/1977 | Eifler et al. | 564/333 |
| 5,679,840 | A | * | 10/1997 | Knofel et al. | 560/347 |
| 5,679,841 | A | * | 10/1997 | Knofel et al. | 560/347 |
| 5,994,570 | A | | 11/1999 | Ogawa et al. | 560/347 |
| 6,031,136 | A | * | 2/2000 | Renbaum et al. | 564/333 |
| 6,140,382 | A | | 10/2000 | Gallus et al. | 521/155 |
| 6,433,219 | B1 | | 8/2002 | Ströfer et al. | 560/347 |
| 2002/0132953 | A1 | | 9/2002 | Strofer et al. | 528/44 |

OTHER PUBLICATIONS

Ullmanns Enzyklopädie der technischen Chemie, 4$^{th}$ Edition, vol. 13, 1977, pp. 347–358, Verlag Chemie GmbH, Weidheim,, "Isocyanate" Dr. Karl–Heinz Eisenmann and Dr. Karl–Friedrich Zenner.

* cited by examiner

*Primary Examiner*—Rabon Sergent
(74) *Attorney, Agent, or Firm*—Joseph C. Gil; Lyndanne M. Whalen

(57) ABSTRACT

Polyisocyanates of the diphenyl methane series having reduced color values are obtained by a) reacting aniline and formaldehyde in the presence of an acid catalyst to form a polyamine, b) neutralizing the reaction mixture containing polyamine with a base, c) separating the neutralized mixture into the aqueous and the organic phases, d) adding a base to the organic phase and then e) phosgenating the resulting polyamine to produce the corresponding polyisocyanate.

6 Claims, No Drawings

PROCESS FOR PRODUCING POLYISOCYANATES OF THE DIPHENYL METHANE SERIES HAVING A REDUCED COLOR VALUE

BACKGROUND OF THE INVENTION

The invention relates to a process for producing polyamines of the diphenyl methane series and to a process for producing polyisocyanates of the diphenyl methane series having a reduced color value obtained by reacting the corresponding polyamine with phosgene.

Polyisocyanates of the diphenyl methane series are isocyanates and mixtures of isocyanates of the following type:

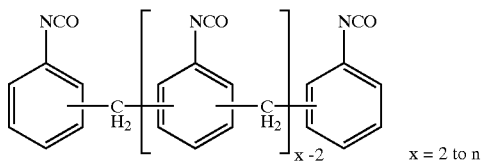

$x = 2$ to $n$

Corresponding polyamines of the diphenyl methane series are compounds and mixtures of compounds of the following type:

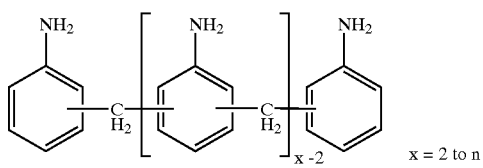

$x = 2$ to $n$

Large scale production of isocyanates by reacting amines with phosgene in solvents is known and described in detail in the literature (see, e.g., Ullmanns Enzyklopädie der technischen Chemie, 4th Edition, Vol. 13, pages 347 to 357, Verlag Chemie GmbH, Weinheim, 1977). The polyisocyanate mixture used as the polyisocyanate component in the production of polyurethane foams and other polyurethane plastics obtained by the polyaddition process, is produced on the basis of this process.

It is generally known that undesirable dyes or coloring components are also formed in this process, and are retained even during further processing to produce polyurethane foams or other polyurethane plastics. Although the inherent color of the polyisocyanate polyaddition products does not adversely affect the mechanical properties thereof, substantially colorless products are desired by the consumer. The extinction at various wavelengths serves as a measure for the coloration of the polyisocyanate.

Therefore, the reduction in the color value of polyisocyanates of the diphenyl methane series has for a long time been the aim of numerous investigations and studies which are described in the literature. Thus, DE-A1-4208359, for example, describes the treatment of such isocyanates with hydrogen in the presence of carrier catalysts. DE-A1-4232769 describes the addition of amines, ureas and antioxidants to the isocyanate. DE-A1-19815055 describes an improvement in the color of polyisocyanates of the diphenyl methane series obtained by irradiation with light over a prolonged period of time. DE-A1-19804915 describes the color reduction of polyisocyanates of the diphenyl methane series by a complicated time- and temperature-graded addition of formaldehyde at the polyamine stage which is then converted into the desired isocyanate by phosgenation.

The drawback of all these procedures is that they are technically complex and/or necessitate the use of auxiliaries or are less efficient.

SUMMARY OF THE INVENTION

The object of the present invention is therefore to provide a technically simple and reliable process for producing polyisocyanates of the diphenyl methane series having low color values. A further object of the present invention is to provide a simple process for producing polyamines of the diphenyl methane series from which polyisocyanates of the diphenyl methane series with low color values can be produced by phosgenation.

These and other objectives which will be apparent to those skilled in the art are accomplished by neutralizing a polyamine-containing reaction mixture with a base, separating the aqueous and organic phases of the neutralized mixture and adding base to the separated organic phase. The separated organic phase to which base has been added may then be phosgenated to produce the corresponding polyisocyanate.

DETAILED DESCRIPTION OF THE INVENTION

The present invention is directed to a process for producing polyamines of the diphenyl methane series, in which a) aniline and formaldehyde are reacted in the presence of an acid catalyst to produce a polyamine and then b) the reaction mixture is neutralized with a base, the aqueous and the organic phases are separated after neutralization and a base is added to the organic phase.

The present invention is also directed to a process for producing polyisocyanates of the diphenyl methane series, in which a) aniline and formaldehyde are reacted in the presence of an acid catalyst to form a polyamine, b) the reaction mixture is neutralized with a base, the aqueous and the organic phases are separated after neutralization and a base is added to the organic phase, and then c) the resulting polyamine is reacted to produce the corresponding polyisocyanate by phosgenation.

The processes of the present invention can be carried out continuously or discontinuously.

Polyisocyanates having low color values can be produced by the process of the invention. Color value as used herein means the measured extinction of a solution of polyisocyanate in monochlorobenzene, containing 2% by weight polyisocyanate, in a layer thickness of 10 mm at ambient temperature against monochlorobenzene at defined wavelengths.

The polyamine or polyamine mixture of the diphenyl methane series used in the process of the invention may be obtained by condensation of aniline and formaldehyde in the presence of an acid catalyst (H. J. Twitchett, Chem. Soc. Rev. 3(2), 209 (1974), W. M. Moore in: Kirk-Othmer Encycl. Chem. Technol., 3rd Edition, New York, 2, 338 to 348 (1978)). It is irrelevant to the present invention whether aniline or formaldehyde is initially mixed in the absence of the acid catalyst and the acid catalyst subsequently added or whether a mixture of aniline and acid catalyst is reacted with formaldehyde.

Suitable polyamine mixtures of the diphenyl methane series are conventionally obtained by condensation of aniline and formaldehyde in the molar ratio 20 to 1.6, preferably 10 to 1.8 and a molar ratio of aniline and acid catalyst of 20 to 1, preferably 10 to 2.

Formaldehyde is conventionally used industrially as an aqueous solution. However, other methylene group-supplying compounds, such as polyoxymethylene glycol, para-formaldehyde or trioxane, may also be used.

Strong organic and preferably inorganic acids can be used as acid catalysts. Suitable acids are, for example, hydrochloric acid, sulphuric acid, phosphoric acid and methane sulphonic acid. Hydrochloric acid is preferably used.

In a preferred embodiment of the process, aniline and acid catalyst are initially mixed. In a further step, this mixture is mixed, optionally after removing heat, with formaldehyde at a temperature between 20° C. and 100° C., preferably at 30° C. to 70° C., in a suitable manner and then subjected to an initial reaction in a suitable residence time apparatus. The initial reaction takes place at a temperature between 20° C. and 100° C., preferably in the temperature range 30° C. to 80° C. After mixing and initial reaction, the temperature of the reaction mixture is brought in stages or continuously and optionally under excess pressure, to a temperature of 100° C. to 250° C., preferably to 100° C. to 180° C., most preferably to a temperature of 100° C. to 160° C.

However, it is also possible in another embodiment of the process to initially mix aniline and formaldehyde in the absence of the acid catalyst, in the temperature range of 5° C. to 130° C., preferably of 40° C. to 100° C., most preferably of 60° C. to 90° C., and to react them. Condensation products of aniline and formaldehyde (so called "aminals") are formed. After the formation of an aminal, the water present in the reaction mixture can be removed by phase separation or other suitable process steps, for example by distillation. The condensation product is then appropriately mixed with the acid catalyst in a further process step and subjected to an initial reaction in a residence time apparatus at 20° C. to 100° C., preferably 30° C. to 80° C. The temperature of the reaction mixture is subsequently brought in stages or continuously and optionally under excess pressure, to a temperature of 100° C. to 250° C., preferably to 100° C. to 180° C., most preferably to a temperature of 100° C. to 160° C.

The reaction of aniline and formaldehyde in the presence of an acid catalyst to form a polyamine of the diphenyl methane series can take place in the presence of additional substances (for example, solvents, salts, organic and inorganic acids).

To work up the acid reaction mixture, the reaction mixture of the prior art is neutralized with a base. According to the prior art, neutralization is conventionally carried out at temperatures of, for example, 90 to 100° C. (H. J. Twitchett, Chem. Soc. Rev. 3(2), 223 (1974)). The hydroxides of alkali and alkaline-earth metal elements, for example, are suitable as bases. Aqueous NaOH is preferably used.

Neutralization is carried out, for example, in such a way that the acidic reaction mixture from the aniline/formaldehyde condensation is mixed with the base and supplied to a residence time apparatus (for example, stirred tank, cascade of stirred-tank reactors, flow tube, circulating reactor). In a suitable residence time apparatus (for example, stirred tanks), the acid condensation mixture and base can also be mixed directly in the residence time apparatus.

According to the prior art, the organic phase can be separated from the aqueous phase by suitable processes (for example, phase separation in a Florentine receiver) after neutralization. The organic and aqueous phase can be separated at the same temperature as neutralization of the acid rearrangement mixture takes place. The product-containing organic phase remaining after separation of the aqueous phase is washed, according to the prior art, to remove salts and excess base. The resulting organic phase is subsequently freed from excess aniline and other substances present in the mixture (for example, other solvents) by suitable separation processes, such as distillation, extraction or crystallization.

In the process of the present invention, neutralization is followed by an additional process step, in which the organic phase is treated with a base. Finally, the polyisocyanates obtained after phosgenation have a reduced color value.

In the process of the present invention, neutralization is carried out, for example, at a temperature corresponding to the prior art, preferably at 90° to 100° C. The aqueous and the organic phase are subsequently separated by one of the conventional methods (for example, by phase separation in a Florentine receiver). After phase separation, the organic phase of the neutralized reaction mixture is treated in a residence time apparatus with a base, for example with one of the hydroxides of the alkali or alkaline-earth metal elements or aqueous solutions thereof, preferably with aqueous sodium hydroxide solution.

The organic phase of the neutralized reaction mixture is preferably treated with the base at a temperature above 60° C., more preferably of 61° C. to 300° C., more particularly preferably 80° C. to 200° C., most preferably 90° C. to 160° C.

The supply or removal of heat may be necessary to adjust the temperature for the treatment of the organic phase of the neutralized reaction mixture with the base. This is guided, in particular, by the desired temperature at which the treatment of the organic phase with the base should take place, but also by the temperature of the organic phase used and the temperature of the base or base solution used. To prevent boiling below a desired temperature, the process may need to be carried out at elevated pressure.

The base used to treat the organic phase is preferably used in quantities greater than 1%, more preferably 2 to 400%, most preferably 5 to 150% of the amount required stoichiometrically for neutralization of the acid catalyst used for the condensation reaction. The organic phase is held in the presence of the base preferably for a residence time of $\geq 0.1$ min, more preferably 0.1 to 180 min, more particularly preferably 2 to 150 min, most preferably 10 to 120 min, at a temperature above 60° C. The organic phase of the neutralized reaction mixture is treated with the base, for example, in such a way that the organic phase is mixed with the base and supplied to a residence time apparatus (for example, stirred tank, cascade of stirred tank reactors, flow tube or circulating reactor). The organic phase and base can also be mixed directly in the residence time apparatus using suitable models thereof.

The effect on the color of the polyisocyanates of the diphenyl methane series is intensified if adequate, thorough mixing of the organic and aqueous phase is achieved in the residence time apparatus. This can be achieved by applying the methods known in the prior art, for example, by using static or dynamic mixers or generating turbulence. After this treatment of the organic phase with base, phase separation is performed, optionally, after addition of water, and the organic phase is supplied to the further working up steps (for example, washing and distillation), thereby obtaining a polyamine of the diphenylmethane series. The NaOH-containing aqueous phase from phase separation can advantageously be introduced into the neutralization stage of the process, optionally, after addition of water and/or NaOH, to adjust the desired base quantity or concentration of base.

The polyamine of the diphenyl methane series (crude MDA) obtained in this way is reacted with phosgene in an inert organic solvent by known methods to form the corresponding isocyanate. The molar ratio of crude MDA to phosgene is expediently calculated such that there is from 1 to 10 mol, preferably 1.3 to 4 mol of phosgene per mol $NH_2$ group in the reaction mixture. Chlorinated, aromatic hydrocarbons, such as monochlorobenzene, dichlorobenzenes, trichlorobenzenes, the corresponding toluenes and xylenes and chloroethylbenzene are suitable inert solvents. Monochlorobenzene, dichlorobenzene or mixtures of these chlorobenzenes, in particular, are used as inert organic solvents. The quantity of solvent is preferably such that the reaction mixture has an isocyanate content of from 2 to 40% by weight, preferably between 5 and 20% by weight, based on the total weight of the reaction mixture. After phosgenation, the excess phosgene, the inert organic solvent, the HCl formed or mixtures thereof are separated from the reaction mixture by suitable processes (for example, by distillation).

The crude MDI produced by the process according to the present invention has considerably reduced coloration. However, further analytical differences may also be detected in the MDI produced (for example, an increased isocyanate group content).

Having thus described the invention, the following Examples are given as being illustrative thereof.

EXAMPLES

Example 1

Comparison Example 1048.9 g aniline and 1026.5 g of a 32.2% aqueous formaldehyde solution were simultaneously added dropwise at 80° C. to 1,000 g aniline within 20 minutes. The mixture was stirred for 10 minutes after the addition was completed and phase separation was subsequently performed at 70° C. to 80° C. A quantity of 623.3 g from the organic phase was cooled to 35° C. and subsequently mixed at this temperature with the remaining organic phase and 626.8 g of a 31.9% aqueous hydrochloric acid within 30 minutes. After the addition had been completed and after a 30 minute post-stirring time at this temperature, the mixture was heated to 60° C. within 10 minutes and held at this temperature for 30 minutes. The mixture was then heated to reflux temperature within 30 minutes and stirred for 10 hours under reflux. The acidic mixture obtained in this way was then mixed with 532.4 g of a 49.6% aqueous sodium hydroxide solution and 730 ml boiling water. After stirring for a further 15 minutes under reflux at approximately 100° C., phase separation was performed at 80° C. to 90° C. and the organic phase was washed 2 more times with 1,000 ml boiling water each time. The organic phase was then freed of excess aniline by distillation under reduced pressure. Of the polyamine obtained in this way, 50 g was dissolved in 255 ml chlorobenzene, heated to 55° C. and added to a solution of 105 g phosgene in 310 ml of chlorobenzene which was kept at 0° C., within 10 s with intensive stirring. The suspension was heated to 100° C. within 45 minutes by passing through phosgene and subsequently heated to reflux temperature within 10 minutes. After a further 10 minutes at this temperature, the solvent was distilled off under reduced pressure until the sump reached a temperature of 100° C. The crude isocyanate was then heated in a distillation apparatus at a pressure of 4 to 6 mbar by a heating bath heated to 260° C. until the first transition of product and then cooled within 5 minutes to ambient temperature. 1.0 g of the isocyanate obtained in this way was dissolved in chlorobenzene and diluted to 50 ml with chlorobenzene. The resulting solution had an extinction of 0.191 against chlorobenzene at a wavelength of 430 nm, at a layer thickness of 10 mm and at ambient temperature.

Example 2

According to the Invention

As in Example 1, an acidic rearrangement mixture was produced with the quantities of aniline, aqueous formaldehyde solution and aqueous hydrochloric acid stated therein and was subsequently neutralized with 532.4 g of 49.6% aqueous sodium hydroxide solution and 730 ml water at approximately 100° C. The phases were separated and the organic phase was heated to reflux with 1,477 g of a 50% aqueous sodium hydroxide solution while stirring for 90 minutes at approximately 140° C. After phase separation, the organic phase was treated further as in Example 1, by washing with water and distillation under reduced pressure. The resulting polyamine of the diphenyl methane series was reacted with phosgene to produce the corresponding polyisocyanate. The extinction at 430 nm by the method described in Example 1 was 0.133 against chlorobenzene.

Example 3

Comparison Example 1,226 g of the organic phase obtained after neutralization of an acidic rearrangement mixture from the large scale production of polyamines of the diphenyl methane series were worked up as in Example 1 by washing three times with water and by distillation under reduced pressure. The resulting polyamine of the diphenyl methane series was reacted with phosgene to produce the corresponding polyisocyanate. The extinction at 430 nm by the method described in Example 1 was 0.114 against chlorobenzene.

Example 4

According to the invention 1,226 g of the organic phase mentioned in Example 3 and obtained after neutralization of an acid rearrangement mixture from the large scale production of polyamine of the diphenyl methane series were heated to reflux with 368 g of 50% aqueous sodium hydroxide solution with stirring for 2 hours at approximately 130° C. After phase separation, the organic phase was further treated as in Example 3 by washing with water and distillation under reduced pressure and the resulting polyamine of the diphenyl methane series was reacted with phosgene to produce the corresponding polyisocyanate. The extinction at 430 nm by the method described in Example 1 was 0.084 against chlorobenzene.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing polyamines of the diphenyl methane series comprising
    a) reacting aniline and formaldehyde in the presence of an acid catalyst to form a polyamine-containing mixture, b) neutralizing the polyamine-containing mixture with a base, c) separating the neutralized mixture into an aqueous phase and an organic phase, and d) adding a base to the organic phase.

2. The process of claim 1 in which the base of step b) and/or step d) is an alkali hydroxide, an alkaline earth hydroxide or an aqueous solution of alkali hydroxide or alkaline earth metal hydroxide.

3. The process of claim 1 in which aqueous NaOH is used as the base of step b) and/or step d).

4. A process for the production of polyisocyanates of the diphenyl methane series comprising a) reacting aniline and formaldehyde in the presence of an acid catalyst to form a polyamine-containing mixture, b) neutralizing the polyamine-containing mixture with a base, c) separating the neutralized mixture into an aqueous phase and an organic phase, d) adding a base to the organic phase, and separating the polyamine, e) phosgenating the polyamine to produce a polyisocyanate.

5. The process of claim 4 in which the base of step b) and/or step d) is an alkali metal hydroxide, an alkaline earth metal hydroxide or an aqueous solution of an alkali metal hydroxide or an alkaline earth metal hydroxide.

6. The process of claim 4 in which aqueous NaOH is used as the base of step b) and/or step d).

\* \* \* \* \*